(12) United States Patent
Wei et al.

(10) Patent No.: US 10,816,503 B2
(45) Date of Patent: Oct. 27, 2020

(54) ELECTROCHEMICAL GAS SENSOR FOR DETECTING HYDROGEN CYANIDE GAS

(71) Applicant: HONEYWELL INTERNATIONAL INC., Morris Plains, NJ (US)

(72) Inventors: Na Wei, Morris Plains, NJ (US); Yuzhong Yu, Morris Plains, NJ (US); Ling Liu, Morris Plains, NJ (US)

(73) Assignee: Honeywell International Inc., Morris Plains, NY (US)

( * ) Notice: Subject to any disclaimer, the term of this patent is extended or adjusted under 35 U.S.C. 154(b) by 54 days.

(21) Appl. No.: 16/317,097

(22) PCT Filed: Jul. 12, 2016

(86) PCT No.: PCT/CN2016/089737
§ 371 (c)(1),
(2) Date: Jan. 11, 2019

(87) PCT Pub. No.: WO2018/010081
PCT Pub. Date: Jan. 18, 2018

(65) Prior Publication Data
US 2019/0317043 A1    Oct. 17, 2019

(51) Int. Cl.
*G01N 27/404*    (2006.01)
*G01N 27/407*    (2006.01)
(Continued)

(52) U.S. Cl.
CPC ....... *G01N 27/4078* (2013.01); *G01N 27/304* (2013.01); *G01N 27/4045* (2013.01);
(Continued)

(58) Field of Classification Search
None
See application file for complete search history.

(56) References Cited

U.S. PATENT DOCUMENTS

| 4,141,800 A | 2/1979 | Breuer et al. |
| 4,227,974 A | 10/1980 | Petersen et al. |

(Continued)

FOREIGN PATENT DOCUMENTS

| CN | 202033323 U | 11/2011 |
| CN | 103336041 A | 10/2013 |

(Continued)

OTHER PUBLICATIONS

EPO machine-generated English language translation of Ping et al. CN 103336041 A, applicaiton published Oct. 2, 2013 (Year: 2013).*

(Continued)

*Primary Examiner* — Alexander S Noguerola
(74) *Attorney, Agent, or Firm* — Alston & Bird LLP

(57) ABSTRACT

An electrochemical hydrogen cyanide sensor (1) comprises a housing (10) comprising an opening (2) allowing gas to enter the sensor (1); an electrolyte disposed within the housing (10); a plurality of electrodes in contact with the electrolyte within the housing (10), wherein the plurality of electrodes comprise a working electrode (5) and a counter electrode (7), and wherein the electrodes comprise a metal catalytic material; and a filter (3) operable to cover the opening (2) of the housing (10), and prevent hydrogen sulfide from reaching the electrodes, wherein the filter (3) comprises silver sulfate layered onto a polytetrafluoroethylene support material.

18 Claims, 3 Drawing Sheets

(51) Int. Cl.
  *G01N 27/30* (2006.01)
  *G01N 33/00* (2006.01)
(52) U.S. Cl.
  CPC ..... *G01N 27/4072* (2013.01); *G01N 27/4074* (2013.01); *G01N 27/4075* (2013.01); *G01N 33/0059* (2013.01)

(56) References Cited

U.S. PATENT DOCUMENTS

| | | | |
|---|---|---|---|
| 4,521,290 A | 6/1985 | Venkatasetty | |
| 4,639,306 A | 1/1987 | Tomasovie et al. | |
| 5,284,566 A * | 2/1994 | Cuomo | G01N 27/4045 204/412 |
| 5,879,527 A | 3/1999 | Kiesele et al. | |
| 5,944,969 A | 8/1999 | Scheffler et al. | |
| 6,284,545 B1 * | 9/2001 | Warburton | G01N 27/4045 422/50 |
| 2010/0012494 A1 * | 1/2010 | Kiesele | G01N 27/4045 204/431 |

FOREIGN PATENT DOCUMENTS

| | | |
|---|---|---|
| CN | 104865251 A | 8/2015 |
| GB | 2369891 B | 4/2003 |

OTHER PUBLICATIONS

Joseph Forrest and Leonard Newman (1973), "Ambient Air Monitoring for Sulfur Compounds," Journal of the Air Pollution Control Association, 23:9, 761-768 (Year: 1973).*
EPO machine-generated English language translation of Feng et al. CN 104865251 A, applicaiton published Aug. 26, 2015 (Year: 2015).*
International Search Report and Written Opinion for Application No. PCT/CN2016/089737 dated Mar. 2, 2017, 9 pages.
Extended European Search Report for Patent Application No. 16908413.4 dated Jan. 17, 2020, 8 pages.
Communication Pursuant to Rules 70(2) and 70a(2) for European Patent Application No. 16908413.4 dated Feb. 4, 2020, 1 page.
Office Action for Chinese Patent Application No. 201680087466.7 dated Jul. 20, 2020, 23 pages.

* cited by examiner

ELECTROCHEMICAL GAS SENSOR FOR DETECTING HYDROGEN CYANIDE GAS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Hydrogen Cyanide (HCN) is used, or can be produced, in many industrial applications. It is extremely toxic, and even relatively small amounts are lethal to humans. In this context, there is an increasing demand for HCN gas sensors for safety monitoring. An HCN gas sensor may be operable to detect the presence of HCN gas and issue an alarm based on the detection. HCN gas sensors may be carried by users, and/or may be placed in locations where there is a potential for HCN gas leakage.

In monitoring for the presence of various gases, other gases such as carbon monoxide (CO), or hydrogen sulfide (H2S) can be present that can also react within the sensor. For example, the working electrode can comprise a catalyst that can catalyze the reaction of both a target gas and an interferent gas. As a result, the presence of the interferent gas may create a cross-sensitivity in the sensor, resulting in the false impression that greater levels of the target gas are present in the ambient gases than are actually present. Due to the danger presented by the presence of various target gases, the threshold level for triggering an alarm can be relatively low, and the cross-sensitivity due to the presence of the interferent may be high enough to create a false alarm for the target gas sensor.

SUMMARY

In an embodiment, an electrochemical hydrogen cyanide (HCN) sensor comprises a housing comprising an opening allowing gas to enter the sensor; an electrolyte disposed within the housing; a plurality of electrodes in contact with the electrolyte within the housing, wherein the plurality of electrodes comprise a working electrode and a counter electrode; and a filter operable to cover the opening of the housing, and prevent hydrogen sulfide (H2S) from reaching the electrodes.

In an embodiment, a method for detecting hydrogen cyanide (HCN), the method comprises receiving an ambient gas into a housing of an HCN sensor, wherein the ambient gas comprises HCN and hydrogen sulfide (H2S), and wherein the HCN sensor comprises a plurality of electrodes in contact with an electrolyte within the housing, wherein the plurality of electrodes comprises a porous working electrode and a counter electrode; filtering the H2S gas from the ambient gas; applying a voltage potential between the counter electrode and the working electrode; contacting the ambient gas with the porous working electrode; allowing the ambient gas to diffuse through the porous working electrode to contact the electrolyte; generating a current between the porous working electrode and the counter electrode in response to a reaction between the ambient gas and the electrolyte at the surface area of the working electrode; and determining a concentration of the HCN in the ambient gas based on the current.

In an embodiment, an electrochemical hydrogen cyanide (HCN) sensor comprises a housing comprising an opening allowing gas to enter the sensor; an electrolyte disposed within the housing; a plurality of electrodes in contact with the electrolyte within the housing, wherein the plurality of electrodes comprise a working electrode and a counter electrode, and wherein the electrodes comprise a metal catalytic material; and a filter operable to cover the opening of the housing, and prevent hydrogen sulfide (H2S) from reaching the electrodes, wherein the filter comprises silver sulfate layered onto a polytetrafluoroethylene (PTFE) support material.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
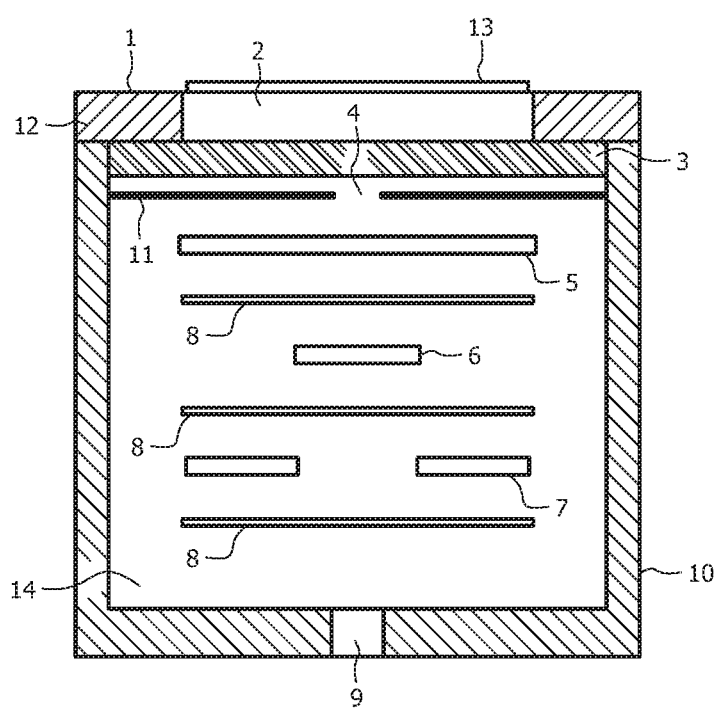
FIG. 1 illustrates a cross-section view of an electrochemical sensor according to an embodiment.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might"

(or other such language) be included or have a characteristic, that particular component or feature is not required to be included or to have the characteristic. Such component or feature may be optionally included in some embodiments, or it may be excluded.

Hydrogen Cyanide (HCN) is used in many industrial applications. It is extremely toxic, and even relatively small amounts are lethal to humans. (Example regulations include OSHA PEL at 10 ppm HCN, and ACGIH TLV at 4.7 ppm HCN.) In this context, there is an increasing demand for HCN gas sensors for safety monitoring. In many cases, there are many other toxic gases in addition to HCN gas, such as hydrogen sulfide ($H_2S$). Currently, there are two types of HCN sensors that are commonly used. One uses gold (Au) as a working electrode, the other uses silver (Ag) as a working electrode. For sensors using Au, $H_2S$ gas often gives a large positive signal more so than HCN on the instrument, 1.5 ppm $H_2S$ results in an about 9 ppm HCN reading, which can trigger a false alarm. For Ag HCN gas sensors, $H_2S$ gas consumes silver to form silver sulfide, thereby reducing the sensor sensitivity and life significantly. $H_2S$ gas not only can cause false alarms, but may also quickly destroy the sensor. Under the conditions where $H_2S$ and HCN gases are present (or leaking), such as in a fire scenario, a large positive signal caused by the $H_2S$ may trigger an HCN detection alarm, and the false alarm may cause panic and inconvenience to users. So far, there is no sensor available that can reduce the cross-sensitivity or poison of $H_2S$ on HCN detectors without affecting the sensor sensitivity and performance.

In some electrochemical sensors, chemical filters may be used to remove or reduce the presence of certain gases in the sensor. However, typical chemical filters may not successfully reduce the cross-sensitivity of $H_2S$ for an HCN detector. For example, a soda lime filter, an activated carbon filter, and/or a rubber charcoal filter may be used to prevent sensor cross-sensitivity to $H_2S$. However, the use of carbon filters may be restricted to only a few types of gas sensors, because activated carbon can absorb a wide range of gases including HCN. Therefore, the use of filters containing soda lime or activated carbon to prevent the cross-sensitivity of $H_2S$ on HCN gas sensors may not be successful, because soda lime or activated carbon can also react with and/or absorb HCN. Another type of filter may include activated alumina impregnated with potassium permanganate operable to absorb $H_2S$ gas, but it also may also absorb HCN gas. Some sensors may use filters containing $Ag_2SO_4$ to reduce the cross-sensitivity to $H_2S$ on sulfur dioxide detectors. However, the $Ag_2SO_4$ filter is prepared by impregnating the substrate by salt solutions, wherein the substrate comprises glass fibers. As is well known in the art, glass fibers typically comprise materials such as $SiO_2$, $Al_2O_3$, $TiO_2$, and $ZrO_2$, which will absorb HCN gas. Therefore, an $Ag_2SO_4$ filter would not work in an HCN gas sensor.

Embodiments described herein include an electrochemical sensor for detection of HCN, where the sensor may comprise a filter operable to remove $H_2S$ gas and not affect sensor sensitivity and performance. The electrochemical sensor may comprise one or more electrodes, such as working, counter and reference electrodes, as well as an electrolyte. The electrochemical sensor may also comprise a filter including silver sulfate layered onto a polytetrafluoroethylene (PTFE) support material, where PTFE has good hydrophobic performance, and has no absorption to HCN gas.

FIG. 1 illustrates a cross-section drawing of an electrochemical sensor 1. The electrochemical sensor 1 generally comprises a housing 10 defining a cavity or reservoir 14 designed to hold an electrolyte solution. A working electrode 5 can be placed between an opening 4 and the reservoir 14. A counter electrode 7 and a reference electrode 6 can be positioned within the reservoir 14. When the gas reacts within the reservoir 14, an electrical current and/or potential can be developed between the electrodes to provide an indication of the concentration of the gas. A reference electrode 6 may also be positioned within the reservoir 14 to provide a reference for the detected current and potential between the working electrode 5 and the counter electrode 7.

The housing 10 defines the interior reservoir 14, and one or more openings 2, 4 can be disposed in the housing to allow a gas to be detected to enter the housing 10. The housing 10 can generally be formed from any material that is substantially inert to the electrolyte and gas being measured. In an embodiment, the housing 10 can be formed from a polymeric material, a metal, or a ceramic. For example, the housing can be formed from a material including, but not limited to, acrylonitrile butadiene styrene (ABS), polyphenylene oxide (PPO), polyvinyl chloride (PVC), polyvinylidene difluoride (PVDF), polystyrene (PS), polypropylene (PP), polyethylene (PE) (e.g., high density polyethylene (HDPE)), polyphenylene ether (PPE), or any combination or blend thereof. In some embodiments, the housing 10 may be formed form a polymer that is resistant to sulfuric acid.

One or more openings 2, 4 can be formed through the housing 10 to allow the ambient gas to enter the housing 10 and/or allow any gases generated within the housing 10 to escape. In an embodiment, the electrochemical sensor 1 may comprise at least one inlet opening 4 to allow the ambient gas to enter the housing 10. The opening 4 can be disposed in a cap 11 when a cap is present and/or in a wall of the housing 10. In some embodiments, the opening 4 can comprise a diffusion barrier to restrict the flow of gas (e.g., HCN, etc.) to the working electrode 5. The diffusion barrier can be created by forming the opening 4 as a capillary and/or a film or membrane can be used to control the mass flow rate through the one or more openings 2, 4.

In an embodiment, the opening 4 may serve as a capillary opening to provide a rate limited exchange of the gases between the interior and exterior of the housing 10. In an embodiment, the opening 4 may have a diameter between about 200 µm and about 1.5 mm, where the opening 4 can be formed using a convention drill for larger openings and a laser drill for smaller openings. The opening 4 may have a length between about 0.5 mm and about 5 mm, depending on the thickness of the cap or housing 10. In some embodiments, two or more openings may be present for the inlet gases. When a membrane is used to control the gas flow into and/or out of the housing 10, the opening diameter may be larger than the sizes listed above as the film can contribute to and/or may be responsible for controlling the flow rate of the gases into and out of the housing 10.

The reservoir 14 comprises the counter electrode 7, the reference electrode 6, and the working electrode 5. In some embodiments, the electrolyte can be contained within the reservoir 14, and the counter electrode 7, the reference electrode 6, and the working electrode 5 can be in electrical contact through the electrolyte. In some embodiments, one or more porous separators 8 or other porous structures can be used to retain the electrolyte in contact with the electrodes. The separators 8 can comprise a porous member that acts as a wick for the retention and transport of the electrolyte between the reservoir and the electrodes while being electrically insulating to prevent shorting due to direct contact between any two electrodes. One or more of the porous separators 8 can extend into the reservoir 14 to provide the electrolyte a path to the electrodes. In an embodiment, a separator 8 can be disposed between the counter electrode 7 and the reference electrode 6, and a separator 8 can be disposed between the reference electrode 6 and the working electrode 5.

One or more of the separators 8 can comprise a nonwoven porous material (e.g., a porous felt member), a woven porous material, a porous polymer (e.g., an open cell foam, a solid porous plastic, etc.), or the like, and is generally chemically inert with respect to the electrolyte and the materials forming the electrodes. In an embodiment, the separators 8 can be formed from various materials that are substantially chemically inert to the electrolyte including, but not limited to, glass (e.g., a glass mat), polymer (plastic discs), ceramics, or the like.

The electrolyte can be any conventional aqueous acidic electrolyte such as sulfuric acid, phosphoric acid, or a neutral ionic solution such as a salt solution (e.g., a lithium salt such as lithium chloride, etc.), or any combination thereof. For example, the electrolyte can comprise sulfuric acid having a molar concentration between about 3 M to about 12 M. Since sulfuric acid is hygroscopic, the concentration can vary from about 10 wt % to about 70 wt % (1 to 11.5 molar) over a relative humidity (RH) range of the environment of about 3% to about 95%. In an embodiment, the electrolyte can comprise phosphoric acid having a concentration in an aqueous solution between about 30% to about 60% $H_3PO_4$ by weight. As another example, the electrolyte can include a lithium chloride salt having about 30% to about 60% LiCl by weight, with the balance being an aqueous solution.

In an embodiment of the sensor 1, the electrolyte may comprise approximately 4 M of sulfur acid and with additive of silver sulfate. In another embodiment of the sensor 1, the electrolyte may comprise propylene carbonate with an addition of lithium perchlorate, with the concentration of lithium perchlorate of approximately 0.4 M.

The working electrode 5 may be disposed within the housing 10. The gas entering the electrochemical sensor 1 can contact one side of the working electrode 5 and pass through the working electrode 5 to reach the interface between the working electrode 5 and the electrolyte. The gas can then react to generate the current indicative of the gas concentration. As disclosed herein, the working electrode 5 can comprise a plurality of layers. The base or substrate layer can comprise a hydrophobic material or a hydrophobically treated material. A catalytic material can be formed as an electrode on one side of the working electrode 5 and placed in contact with the electrolyte. In an embodiment, the catalytic material in the working electrode may comprise gold to provide for the detection of acrylonitrile.

In an embodiment, the working electrode 5 can comprise a porous substrate or membrane as the base layer. The substrate can be porous to the gas of interest, which can comprise acrylonitrile. In an embodiment, the substrate can comprise a carbon paper formed of carbon or graphite fibers. In some embodiments, the substrate can be made to be electrically conductive through the addition of a conductive material such as carbon. The use of carbon may provide a sufficient degree of electrical conductivity to allow the current generated by the reaction of the gas with the electrolyte at the surface of the working electrode 5 to be detected by a lead coupled to the working electrode 5. Other electrically conductive substrates may also be used such as carbon felts, porous carbon boards, and/or electrically conductive polymers such as polyacetylene, each of which may be made hydrophobic as described below. Alternatively, an electrically conductive lead can be coupled to the catalytic layer to electrically couple the catalytic material to the external circuitry, as described in more detail herein. In an embodiment, the substrate can be between about 5 mils to about 20 mils thick in some embodiments.

The porous substrate can be hydrophobic to prevent the electrolyte from passing through the working electrode 5. The substrate can be formed from a hydrophobic material, or the substrate can be treated with a hydrophobic material. In an embodiment, the substrate can be made hydrophobic through the impregnation of the substrate with a hydrophobic material such as a fluorinated polymer (e.g., PTFE, etc.). In some embodiments, the substrate or membrane can comprise GEFC-IES (e.g., the copolymer of perfluorosulfonic acid and PTFE, which is commercially available from Golden Energy Fuel Cell Co., Ltd.), Nafion® (a copolymer of polytetrafluoroethylene and perfluoro-3,6-dioxa-4-methyl-7-octene-sulfonic acid, which is commercially available from Dupont™), or pure or nearly pure polytetrafluoroethylene (PTFE). The impregnation process can include disposing a hydrophobic material containing solution or slurry on the substrate using a dipping, coating, or rolling process. Alternatively, a dry composition such as a powder can be applied to the substrate. In some embodiments, an optional sintering process can be used to infuse the hydrophobic material into the substrate to create the hydrophobic base layer for the working electrode 5, where both sides of the hydrophobic base layer are hydrophobic. The sintering process can cause the hydrophobic polymer to bond or fuse with the carbon of the substrate to securely bond the hydrophobic material to the substrate.

In some embodiments, the sensor 1 may comprise a filter 3 deposited above the opening 4 of the sensor 1, operable to filter a targeted gas. For example, the filter 3 may be operable to remove and/or absorb $H_2S$ gas. In some embodiments, the filter may comprise silver sulfate layered onto a substrate of PTFE powder.

The preparation method of the filter 3 may comprise grinding the silver sulfate and then, applying the silver sulfate to a PTFE emulsion, and stirring the mixture. In some embodiments, the mixture may comprise approximately 3 grams of silver sulfate and approximately 8 grams of the PTFE emulsion. Then, the mixture may be dried to form the filter 3, for example at approximately 200° C. for approximately 2 hours.

In fabricating the electrochemical HCN sensor 1, a separator 8 may be first placed within housing 10. The counter electrode 7 may then be placed into housing 10. Another separator 8 may preferably then be placed within housing 10, followed by reference electrode 6. Yet another separator 8 may be subsequently placed within housing 10 followed by working electrode 5. The working electrode 5 may be inserted face down whereas the counter electrode 7 may be oriented face up. After placement of the working electrode 5 within the housing 10, the perimeter of the working electrode 5 may be heat sealed to a cap 11 which comprises the opening 4. Then, the filter 3 may be placed against the cap 11, which may be wrapped by a membrane. In some embodiments, a top cover 12 and dust cover 13 may be placed above the filter 3. The top cover 12 may also comprise an opening 2, which may be larger than opening 4.

The interior of housing 10 may then be filled with an electrolyte via an opening 9 in the housing 10. Upon filling of the interior of housing 10 with electrolyte, opening 9 may be sealed, optionally via heat sealing using a diffusion barrier through which gas is mobile but through which the electrolyte is substantially immobile. An example of a diffusion barrier suitable for use in the present invention is a Zintex® film. The separators 8 operate to prevent physical contact of the electrodes while allowing the liquid electrolyte to contact the electrodes, thereby providing ionic connection between working electrode 5 and counter electrode 7. The separators 8 may comprise at least one material selected for the group consisting of fiberglass, fumed $SiO_2$, $Al_2O_3$, $TiO_2$, and $ZrO_2$.

In some embodiments, a metal catalyst may be incorporated into one or more of the electrodes. The metal catalyst can be chosen from Au and Ag. And the corresponding electrolyte can be chosen from sulfuric acid with an additive of silver sulfate, and propylene carbonate with an addition of lithium perchlorate.

An exemplary Au electrode may comprise a substrate, and a carbon supported gold catalyst deposited on the substrate. In some embodiments, the carbon supported gold catalyst may comprise 3-10% by weight of a hydrophilic material, 60-87% by weight of gold, and 10 to 30% by weight of a hydrophobic fluoropolymer blocking agent. In some embodiments, the carbon supported gold catalyst may include a hydrophilic aerogel with a weight percent of 5-8%, a hydrophobic fluoropolymer adhesive with a weight percent of 12-28%, gold with a weight percent of 65-80%, and carbon particles with the weight percent of 0-8%.

The carbon support may be solid, porous, absorbent carbon of any desired shape, form and size onto which the gold catalyst is deposited. Such electrodes may be prepared for example by impregnating the absorbent carbon with a solution of a gold salt decomposable to gold oxide, heating the impregnated carbon at an elevated temperature sufficient to effect said decomposition to the oxide followed by heating gold in the presence of hydrogen to reduce the gold oxide to the catalytically active free metal. The preferred electrodes may comprise carbon particles containing catalytic amounts of gold provided thereon by any suitable technique known in the art of catalyst preparation. A method of forming the catalyst may involve forming a solution of metallic gold or a salt thereof, impregnating carbon particles with the resulting solution, drying the impregnated carbon particles followed by heating at elevated temperatures, usually of at least 500° F., optionally 600° F.-800° F. in the presence of a reducing gas, such as hydrogen, so as to ensure conversion of the gold salt to its free metal state and provide an active catalyst. The carbon employed as the support can be any of the carbons conventionally employed as supports in the catalyst art.

The electrochemically active surface of one or more of the electrodes may comprise silver (Ag). The electrode(s) may be fabricated via deposition of an ink comprising silver metal powder and a dispersed Teflon® powder upon a Zintex® membrane. The ink may be deposited via silk screening upon a Zintex® film as known in the art in connection with deposition of electrochemically active materials upon GoreTex® films. Zintex® films were found to provide a good support for the electrochemically active material. The ink may also be deposited using hand painting techniques as known in the art. Some electrodes may be fabricated via silk screening a silver metal ink upon a Zintex® membrane. In some embodiments, a film of electrochemically active material having a thickness in the range of approximately 1 mil to 10 mil (or 0.025 mm to 0.25 mm) may be deposited upon the electrodes of the present disclosure. In some embodiments, the silver powder used to form the electrodes may comprise nanopowder.

Figure 2A:
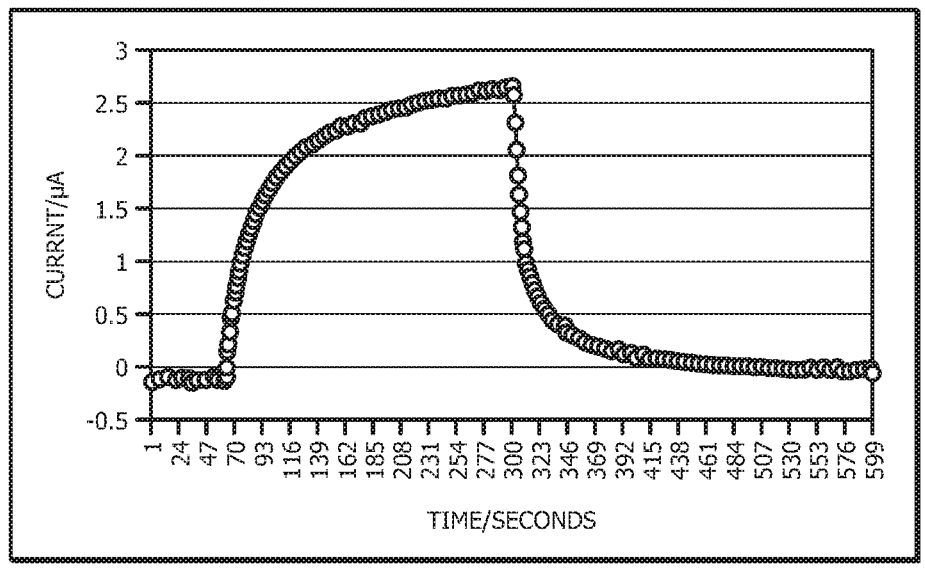
FIGS. 2A-2B illustrate testing results of exposing two electrochemical sensors to HCN gas according to an embodiment.
Figure 2B:
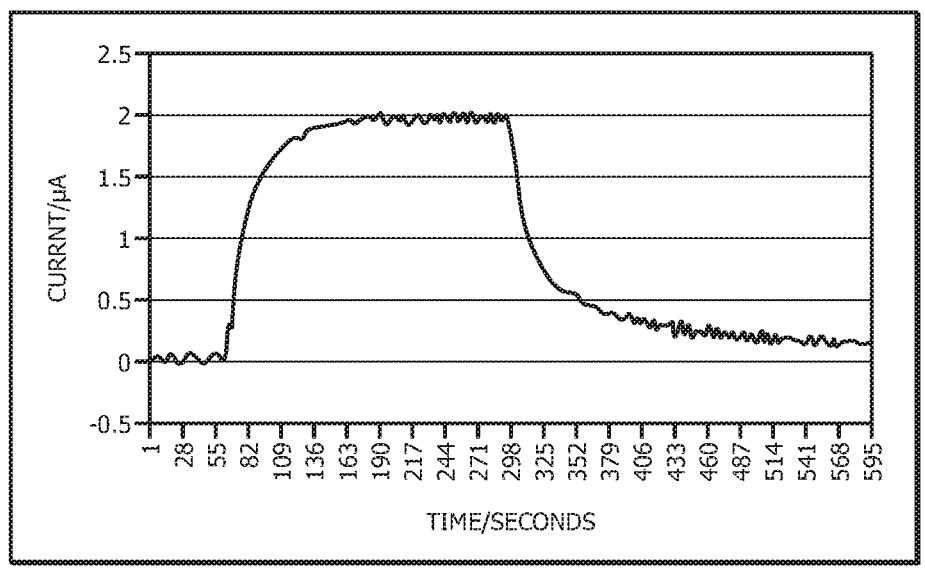

FIGS. 2A-2B illustrate the results of testing two HCN electrochemical sensors, wherein a first sensor is illustrated in FIG. 2A and a second sensor is illustrated in FIG. 2B. The first sensor, illustrated in FIG. 2A, may comprise an electrochemical HCN sensor including Au electrodes and an electrolyte of approximately 4 M of sulfur acid and with an additive of silver sulfate. The second sensor, illustrated in FIG. 2B, may comprise an electrochemical hydrogen cyanide sensor including Ag electrodes and an electrolyte of propylene carbonate with an addition of lithium perchlorate.

In FIGS. 2A-2B, the sensors have been exposed to approximately 10 ppm HCN. As shown in both graphs, the current over time as the sensors are exposed to the HCN gas increases to a level where the current may indicate the presence of HCN, thereby activating a notification and/or alarm by the sensor. In other words, the filter materials incorporated into the sensors may not affect the ability of the sensors to sufficiently detect and indicate the presence of the HCN gas.

Figure 3A:
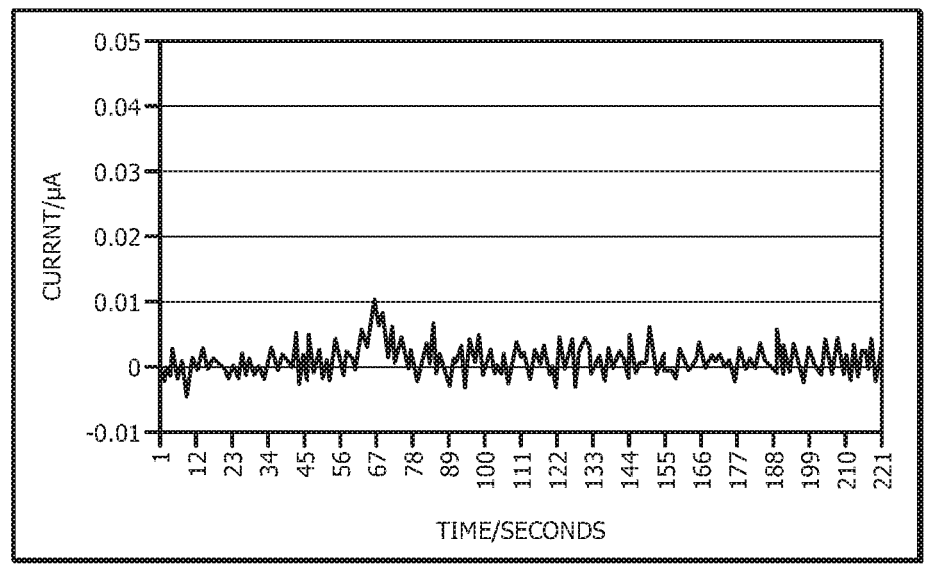
FIGS. 3A-3B illustrate testing results of exposing two electrochemical sensors to $H_2S$ gas according to an embodiment.
Figure 3B:
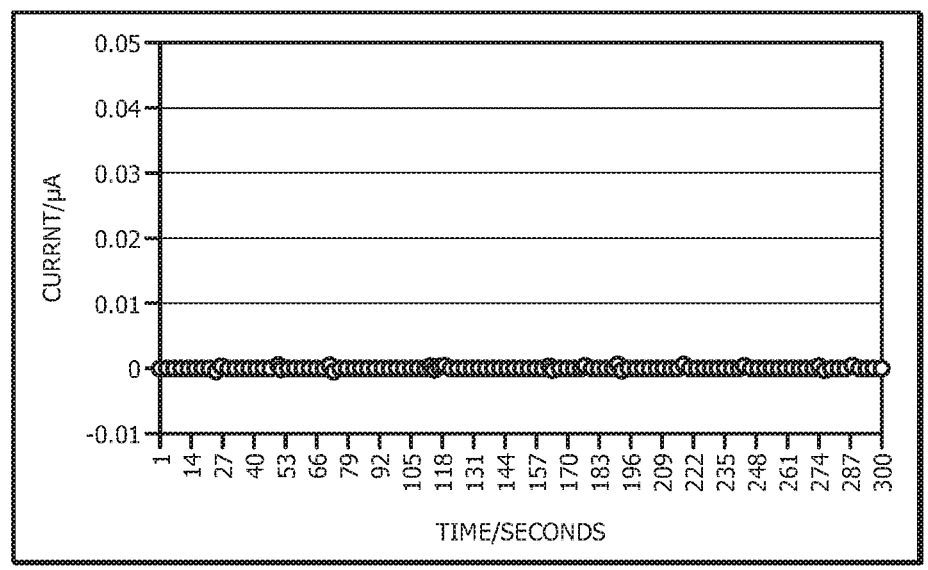

FIGS. 3A-3B illustrates the results of testing the same two HCN electrochemical sensors as described in FIGS. 2A-2B, where the sensors may be exposed to approximately 15 ppm $H_2S$ gas. As shown in both graphs, the $H_2S$ gas does not increase the current reading to a level that would cause a false alarm in the sensor. For example, the current readings caused by exposure to $H_2S$ gas may be less than approximately 1% of the current readings caused by exposure to HCN gas. In other words, a ratio of 1) a sensitivity of the sensor to HCN to 2) a sensitivity of the sensor to $H_2S$ is greater than about 100. Therefore, the filter material incorporated into the sensors may sufficiently remove (or block) the $H_2S$ from the sensor.

In a first embodiment, an electrochemical hydrogen cyanide (HCN) sensor comprises a housing comprising an opening allowing gas to enter the sensor; an electrolyte disposed within the housing; a plurality of electrodes in contact with the electrolyte within the housing, wherein the plurality of electrodes comprise a working electrode and a counter electrode; and a filter operable to cover the opening of the housing, and prevent hydrogen sulfide (H2S) from reaching the electrodes.

A second embodiment can include the sensor of the first embodiment, wherein the filter comprises silver sulfate layered onto a polytetrafluoroethylene (PTFE) support material.

A third embodiment can include the sensor of the first or second embodiment, wherein the filter is formed by grinding the silver sulfate; applying the silver sulfate to a PTFE emulsion; stirring the mixture; and drying the mixture.

A fourth embodiment can include the sensor of the third embodiment, wherein the filter comprises approximately 3 grams of silver sulfate and approximately 8 grams of PTFE.

A fifth embodiment can include the sensor of any of the first to fourth embodiments, wherein at least one of the electrodes comprises a gold (Au) catalytic material.

A sixth embodiment can include the sensor of the fifth embodiment, wherein the electrolyte comprises sulfuric acid with an additive of silver sulfate.

A seventh embodiment can include the sensor of any of the first to sixth embodiments, wherein at least one of the electrodes comprises a silver (Ag) catalytic material.

An eighth embodiment can include the sensor of any of the first to seventh embodiments, wherein the electrolyte comprises propylene carbonate with an addition of lithium perchlorate.

A ninth embodiment can include the sensor of any of the first to eighth embodiments, wherein the sensor is configured to detect HCN, and wherein a ratio of 1) a sensitivity of the sensor to HCN to 2) a sensitivity of the sensor to $H_2S$ is greater than about 100.

A tenth embodiment can include the sensor of any of the first to ninth embodiments, wherein the electrodes comprise a planar arrangement.

An eleventh embodiment can include the sensor of any of the first to ninth embodiments, wherein the electrodes comprise a stacked arrangement.

In a twelfth embodiment, a method for detecting hydrogen cyanide (HCN), the method comprises receiving an ambient gas into a housing of an HCN sensor, wherein the ambient gas comprises HCN and hydrogen sulfide (H2S), and wherein the HCN sensor comprises a plurality of electrodes in contact with an electrolyte within the housing, wherein the plurality of electrodes comprises a porous working electrode and a counter electrode; filtering the H2S gas from the ambient gas; applying a voltage potential between the counter electrode and the working electrode; contacting the ambient gas with the porous working electrode; allowing the ambient gas to diffuse through the porous working electrode to contact the electrolyte; generating a current between the porous working electrode and the counter electrode in response to a reaction between the ambient gas and the electrolyte at the surface area of the working electrode; and determining a concentration of the HCN in the ambient gas based on the current.

A thirteenth embodiment can include the method of the twelfth embodiment, wherein filtering the $H_2S$ gas from the ambient gas comprises passing the ambient gas through a filter comprising silver sulfate layered onto a polytetrafluoroethylene (PTFE) support material.

A fourteenth embodiment can include the method of any of the twelfth to thirteenth embodiments, further comprising forming the filter by grinding the silver sulfate; applying the silver sulfate to a PTFE emulsion; stirring the mixture; and drying the mixture.

A fifteenth embodiment can include the method of the any of the twelfth to fourteenth embodiments, wherein the filter comprises approximately 3 grams of silver sulfate and approximately 8 grams of PTFE.

A sixteenth embodiment can include the method of any of the twelfth to fifteenth embodiments, wherein the sensor is configured to detect HCN, and wherein a ratio of 1) a sensitivity of the sensor to HCN to 2) a sensitivity of the sensor to $H_2S$ is greater than about 100.

A seventeenth embodiment can include the method of any of the twelfth to fifteenth embodiments, wherein at least one of the electrodes comprises a gold (Au) catalytic material.

An eighteenth embodiment can include the method of any of the twelfth to seventeenth embodiments, wherein at least one of the electrodes comprises a silver (Ag) catalytic material.

A nineteenth embodiment can include the method of any of the twelfth to eighteenth embodiments, wherein the electrolyte comprises one of: propylene carbonate with an addition of lithium perchlorate, or sulfuric acid with an additive of silver sulfate.

In a twentieth embodiment, an electrochemical hydrogen cyanide (HCN) sensor comprises a housing comprising an opening allowing gas to enter the sensor; an electrolyte disposed within the housing; a plurality of electrodes in contact with the electrolyte within the housing, wherein the plurality of electrodes comprise a working electrode and a counter electrode, and wherein the electrodes comprise a metal catalytic material; and a filter operable to cover the opening of the housing, and prevent hydrogen sulfide (H2S) from reaching the electrodes, wherein the filter comprises silver sulfate layered onto a polytetrafluoroethylene (PTFE) support material.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises," "includes," and "having" should be understood to provide support for narrower terms such as "consisting of," "consisting essentially of," and "comprised substantially of." Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. An electrochemical hydrogen cyanide (HCN) sensor comprising:
   a housing comprising an opening allowing gas to enter the sensor;
   an electrolyte disposed within the housing;
   a plurality of electrodes in contact with the electrolyte within the housing, wherein the plurality of electrodes comprises a working electrode and a counter electrode; and
   a filter operable to cover the opening of the housing, and prevent hydrogen sulfide ($H_2S$) from reaching the electrodes, wherein the filter comprises silver sulfate layered onto a polytetrafluoroethylene (PTFE) support material.

2. The sensor of claim 1, wherein the filter comprises a dried mixture of ground silver sulfate and PTFE.

3. The sensor of claim 1, wherein the filter comprises approximately 3 grams of silver sulfate and approximately 8 grams of PTFE.

4. The sensor of claim 1, wherein at least one of the electrodes comprises a gold (Au) catalytic material.

5. The sensor of claim 4, wherein the electrolyte comprises sulfuric acid with an additive of silver sulfate.

6. The sensor of claim 1, wherein at least one of the electrodes comprises a silver (Ag) catalytic material.

7. The sensor of claim 6, wherein the electrolyte comprises propylene carbonate with an addition of lithium perchlorate.

8. The sensor of claim 1, wherein the sensor is configured to detect HCN, and wherein a ratio of 1) a sensitivity of the sensor to HCN to 2) a sensitivity of the sensor to $H_2S$ is greater than about 100.

9. The sensor of claim 1, wherein the electrodes comprise a planar arrangement.

10. The sensor of claim 1, wherein the electrodes comprise a stacked arrangement.

11. A method for detecting hydrogen cyanide (HCN), the method comprising:
   receiving an ambient gas into a housing of an HCN sensor, wherein the ambient gas comprises HCN and hydrogen sulfide ($H_2S$), and wherein the HCN sensor comprises a plurality of electrodes in contact with an electrolyte within the housing, wherein the plurality of electrodes comprises a porous working electrode and a counter electrode;
   filtering the $H_2S$ gas from the ambient gas, wherein filtering comprises passing the ambient gas through a filter comprising silver sulfate layered onto a polytetrafluoroethylene (PTFE) support material;
   applying a voltage potential between the counter electrode and the porous working electrode;
   contacting the ambient gas with the porous working electrode;
   allowing the ambient gas to diffuse through the porous working electrode to contact the electrolyte;
   generating a current between the porous working electrode and the counter electrode in response to a reaction between the ambient gas and the electrolyte at a surface area of the porous working electrode; and
   determining a concentration of the HCN in the ambient gas based on the current.

12. The method of claim 11, further comprising forming the filter by grinding the silver sulfate; applying the silver sulfate to a PTFE emulsion to form a mixture; stirring the mixture; and drying the mixture.

13. The method of claim 12, wherein at least one of the electrodes comprises a silver (Ag) catalytic material.

14. The method of claim 12, wherein the electrolyte comprises one of: propylene carbonate with an addition of lithium perchlorate, or sulfuric acid with an additive of silver sulfate.

15. The method of claim 11, wherein the filter comprises approximately 3 grams of silver sulfate and approximately 8 grams of PTFE.

16. The method of claim 11, wherein the sensor is configured to detect HCN, and wherein a ratio of 1) a sensitivity of the sensor to HCN to 2) a sensitivity of the sensor to $H_2S$ is greater than about 100.

17. The method of claim 11, wherein at least one of the electrodes comprises a gold (Au) catalytic material.

18. An electrochemical hydrogen cyanide (HCN) sensor comprising:
   a housing comprising an opening allowing gas to enter the sensor;
   an electrolyte disposed within the housing;
   a plurality of electrodes in contact with the electrolyte within the housing, wherein the plurality of electrodes comprises a working electrode and a counter electrode, and wherein the electrodes comprise a metal catalytic material; and
   a filter operable to cover the opening of the housing, and prevent hydrogen sulfide ($H_2S$) from reaching the electrodes, wherein the filter comprises silver sulfate layered onto a polytetrafluoroethylene (PTFE) support material.

* * * * *